United States Patent
Handte et al.

(10) Patent No.: US 10,025,088 B2
(45) Date of Patent: Jul. 17, 2018

(54) ASSEMBLY FOR A VIDEO ENDOSCOPE

(71) Applicant: RICHARD WOLF GMBH, Knittlingen (DE)

(72) Inventors: René Handte, Vaihingen/Enz (DE); Rudolf Heimberger, Oberderdingen (DE)

(73) Assignee: RICHARD WOLF GMBH, Knittlingen (DE)

(*) Notice: Subject to any disclaimer, the term of this patent is extended or adjusted under 35 U.S.C. 154(b) by 260 days.

(21) Appl. No.: 14/768,059

(22) PCT Filed: Feb. 14, 2014

(86) PCT No.: PCT/EP2014/052914
§ 371 (c)(1),
(2) Date: Aug. 14, 2015

(87) PCT Pub. No.: WO2014/125070
PCT Pub. Date: Aug. 21, 2014

(65) Prior Publication Data
US 2015/0378144 A1    Dec. 31, 2015

(30) Foreign Application Priority Data
Feb. 15, 2013 (DE) .................. 10 2013 202 516

(51) Int. Cl.
*A61B 1/05* (2006.01)
*G02B 23/24* (2006.01)
*H04N 5/225* (2006.01)
*A61B 1/00* (2006.01)
*A61B 1/005* (2006.01)
*H01L 27/146* (2006.01)

(52) U.S. Cl.
CPC .......... *G02B 23/2484* (2013.01); *A61B 1/005* (2013.01); *A61B 1/00018* (2013.01); *A61B 1/00131* (2013.01); *A61B 1/05* (2013.01); *G02B 23/2407* (2013.01); *H01L 27/14601* (2013.01); *H04N 5/2251* (2013.01); *H04N 5/2253* (2013.01); *H04N 2005/2255* (2013.01)

(58) Field of Classification Search
CPC ..................................................... A61B 1/05
See application file for complete search history.

(56) References Cited

U.S. PATENT DOCUMENTS

| 6,635,865 B1 | 10/2003 | Soltyk |
| 2004/0167378 A1 | 8/2004 | Ando |
| 2005/0056457 A1* | 3/2005 | Gall ............... H05K 1/0281 174/254 |
| 2007/0171012 A1 | 7/2007 | Fujimori et al. |

(Continued)

FOREIGN PATENT DOCUMENTS

| EP | 2 677 736 A1 | 12/2013 |
| JP | S56 144673 A | 11/1981 |

(Continued)

*Primary Examiner* — Renee Chavez
(74) *Attorney, Agent, or Firm* — McGlew and Tuttle, P.C.

(57) ABSTRACT

A subassembly for a video endoscope with a picture-recording sensor (9) which is electrically conductively arranged on a flexible circuit board (8) which next to the sensor (9) is bent at least at one side and is conductively connected to at least one electrical cable proximally of the sensor (9).

20 Claims, 5 Drawing Sheets

(56) References Cited

U.S. PATENT DOCUMENTS

2011/0249106 A1* 10/2011 Makino ................ H04N 5/2254
                                                              348/76
2012/0310043 A1     12/2012 Hu et al.
2014/0078287 A1*  3/2014 Ichihashi ............... A61B 1/051
                                                              348/82

FOREIGN PATENT DOCUMENTS

JP          2011 217887 A       11/2011
JP        WO 2012160669 A1 *   11/2012  ............. A61B 1/051
WO         2009/041724 A1       4/2009

* cited by examiner

ASSEMBLY FOR A VIDEO ENDOSCOPE

CROSS REFERENCE TO RELATED APPLICATIONS

This application is a United States National Phase Application of International Application PCT/EP2014/052914 filed Feb. 14, 2014 and claims the benefit of priority under 35 U.S.C. § 119 of German Patent Application 10 2013 202 516.5 filed Feb. 15, 2013 the entire contents of which are incorporated herein by reference.

FIELD OF THE INVENTION

The invention relates to a subassembly for a video endoscope, with a picture-recording (image capturing) sensor.

BACKGROUND OF THE INVENTION

With regard to video endoscopes, it is counted as belonging to the state of the art to place a subassembly consisting of a picture sensor, capacitor, circuit board and cable in the distal region directly behind the lens (objective). The picture which is produced by the lens is projected onto the sensor and the signals are led via cables led through the endoscope shank, to the electronics which are arranged at the proximal side. Such endoscopes or technoscopes are also known under the term "chip-on-the-tip endoscopes". Thereby, there are various construction types, and thus the picture sensor can be arranged in a standing or lying manner. With endoscopes of this construction type, one always strives to keep the cross-sectional dimensions small, in order to be able to get through the smallest possible openings. However, the smaller the diameter of the endoscope, the longer becomes the construction length in the distal end region, which is particularly disadvantageous with flexible endoscopes, since the endoscopes are rigid, i.e. not flexible, in the end region, in which this subassembly is arranged. This problem does not occur with rigid endoscopes, but one constantly strives to use the constructionally identical subassemblies wherever possible, independently of the construction form.

SUMMARY OF THE INVENTION

Against this background, it is an object of the invention to design a subassembly which is of the known type and is for a video endoscope, such that one the one hand an as small as possible construction size with respect to the specified sensor size, thus an as small as possible cross-sectional dimension is achieved and on the other hand a short construction length. An inexpensive manufacture and an application in rigid as well as flexible endoscopes are moreover to be possible.

The subassembly according to the invention, for a video endoscope, comprises a picture-recording sensor which is arranged in an electrically conductive manner on a flexible circuit board, said circuit board being bent next to the sensor at least at one side and being conductively connected to at least one electrical cable proximally of the sensor. The basic concept of the present invention is thus to attach the sensor as well as the cable or cables by way of a flexible circuit board, as is typically manufactured with so-called "thin-layer technology", wherein the circuit board forms the conductive connections between the sensor and cable connections, and the contacting of the circuit board is advantageously effected from only one side, so that the sensor as well as cable connections can be contacted on the same side, but by way of bending the circuit board are spatially located on different planes, typically the cable connections proximally of the sensor. By way of this, it is possible to create a very compact and small subassembly which is moreover inexpensively manufacturable. Thereby, the contact surfaces necessary for the sensor and cables as well as, as the case may be, further contact surfaces for electronic components are created by way of a layer-wise construction. The electrical circuit is integrated into this layer-wise construction, so that the circuit board with all necessary conductors, through-contacts, the circuit, the insulation and the solder pads can have a thickness between 40 and 100 μm. Thereby, all contacts lie at only one side and thus it is only due to the bending that the contacting proximally of the sensor is possible in the first place. Thereby, the construction of the circuit board on a planar plate, for example a glass plate can be effected in a layered manner, wherein the equipping with components is advantageously effected likewise directly on this plate. The circuit board can be folded together in a very compact manner by way of bending the circuit board at locations which are advantageously characterized by markings, by which means a spatially compact subassembly with the smallest possible dimensions, and this being the case in the radial as well as axial direction, is obtained from the relatively long circuit board which is equipped with the sensor and further electronic components as the case may be.

The circuit board apart from the sensor advantageously comprises at least one further electronic component which is arranged on the bent part of the circuit board proximally, which is to say on the proximal side, of the sensor. Such a component is typically a capacitor which is necessary in this proximal subassembly part and has a comparatively large spatial requirement. This capacitor is therefore preferably arranged on the circuit board next to the sensor and is brought proximally of the sensor by way of bending the circuit board.

The subassembly according to the invention can particularly advantageously be formed by a longitudinally extended, narrow circuit board which roughly has the width of the sensor and is bent in a multiple manner and at two sides of the sensor, preferably at sides which are away from one another, so that a slim body results, whose face side is formed by the sensor.

It is to be understood that advantageously only a part of the circuit board is bent at one side, in the case of a lying arrangement of the sensor.

According to an advantageous further development of the invention, a core, about which the circuit board is bent and which is arranged in the region flush with the sensor at the rear of the circuit board is provided, in order to be able to bend the circuit board about 180°, in particular without destruction.

Moreover, it is useful to design the circuit board in a reinforced manner in the region of the sensor. For this, according to an advantageous further development, the circuit board at the rear is provided with reinforcement means in the region where the sensor is arranged at the front. Such reinforcement means can be formed by a support body, which e.g. is bonded or fixed in another suitable manner, at the rear of the circuit board, and thereby the support body and the core are preferably formed by the same body.

However, an even more compact construction results if the circuit board is bent without a support body.

Thereby, it is particularly advantageous if the circuit board carries the sensor and further electronic components and connection only on one circuit board side, since a particularly thin and advantageous single-layer circuit board can then be used. According to the invention, the subassembly comprises a preferably single-layer flex circuit board, which has a thickness between 40 µm and 100 µm, for example 60 µm. Such extremely thin circuit boards can be bent with particularly tight radii of curvature, and specifically also above 90° and more, so that quasi a folding of the circuit board is possible, by which means the constructional volume can be further reduced. According to the invention, one can bend such an extremely thin and flexible circuit board in a bending radius which corresponds to half to twice the thickness of the circuit board. The bending radius advantageously even corresponds to 0.8-fold to 1.2-fold the circuit board thickness, so that in the case of a circuit board thickness of 40 µm, one can also envisage an extremely small bending radius of 40 µm.

According to an advantageous further development of the invention, at least one recess is provided in the region of a bending, in order to reduce the bending stress within the circuit board in this region. Usefully, several recesses which are arranged next to one another and which preferably have a rounded contour and can thus introduce forces into the remain web regions in a continuous manner are usefully provided in the bending region. If no space for such a recess is present in the bending region on account of strip conductors, it is then recommended to provide laterally open recesses at least in the edge regions, so that the circuit board in the bending region has a lower width than in the remaining region.

According to an advantageous further development of the invention, the circuit board parts which bear on one another at the rear are advantageous connected to one another by way of bonding, so that a greater stability is given before the molding (casting) of the subassembly.

A particularly compact subassembly and one which is envisaged for an arrangement with a standing sensor results if the circuit board according to an advantageous further development is bent at least at one side next to the sensor by about 180°, then runs parallel to the sensor and comprises an end section which is bent proximally from this by about 90° and which connects to the section parallel to the sensor. Surfaces then yet result on the circuit board by design, and these can be used for further components or connections. Such a further component in particular can be a capacitor which is then advantageously arranged in an electrically conductive manner in the end section on the circuit board, thus utilises that space between the circuit board and the side which is formed by the 180° bend, thus the free space at the rear of the sensor on the other side of the circuit board.

An alternative design according to the invention envisages bending the circuit board at a side next to the sensor by 180° and at the opposed side next to the sensor by 90°, wherein the circuit board part bent by 180° is led up to the rear side of the circuit board part bent by 90° and there is likewise proximally bent by 90°. The circuit board parts from there then run proximally in a manner bearing on one another (contacting one another) at the rear. The arrangement is thereby preferably rectangular-wave-shaped, wherein electronic components are arranged in the free spaces encompassed by the waves. According to the invention, a free space in the simplest form can be formed in the manner of a wave trough which at one side is formed by the circuit board part bent by 180° next to the sensor, and at the other side as well as the lower side by the two circuit board parts running in a manner bearing on one another at the rear. A large capacitor for example can be arranged in the free space such that this seen in the axis direction of the subassembly is arranged within the outer contour of the subassembly which is formed by the sensor. If further electronic components are to be arranged, then these can either be arranged next to one another or in adjacent free spaces if the circuit board parts are bent in a rectangular-wave-shaped manner. Electronic components can be connected to the circuit board in an electrically conductive manner, just as with the electrical connections which are arranged in an end section, in the respective free spaces, be it within a wave trough or within a wave peak, due to the fact that the circuit board parts bear on one another at the rear.

The electrical connection is preferably not effected via a common cable, but via several single-conductor (singe-core) cables which are electrically conductively connected to solder pads arranged on one or both end sections of the circuit board. It is possible to design the connection of the electric conductors to the circuit board in a very short manner due to the use of individual conductors (leads) instead of a compact and ready-manufactured cable composite. This is rendered possible due to the fact that individual leads/conductors can be stripped in a very short manner and soldered to the circuit board, which is not possible with a compact multi-conductor cable, with which the individual conductors are fixedly bound.

According to a further development of the invention, one envisages either only the cables or however preferably the cable ends at the circuit board side and the end sections of the circuit board being surrounded by a shielding flexible sleeve (sheath), in order to group together and bundle the multitude of these single-conductor or few-conductor cables.

The circuit board can alternatively also be led up to the proximal-side end of the video endoscope and thus replace the cables in this region, and the contacting is then effected in the region of the proximal-side shank end. The lens is advantageously attached directly on the sensor. This complete subassembly, consisting, as the case may be, of the lens, the sensor, the circuit board and the cable ends on the circuit board side and with the shielding flexible sleeve is then molded in plastic in a surrounding housing, in order to fix the components to one another and simultaneously protect them from external influences.

The subassembly according to the invention is provided for integration at the distal end of an endoscope with a rigid or flexible shank, wherein the electrical connection cables are led through the shank or however the circuit board itself forms the lead connections in this region.

The invention is hereinafter explained in more detail by way of one embodiment example which is represented in the drawing. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
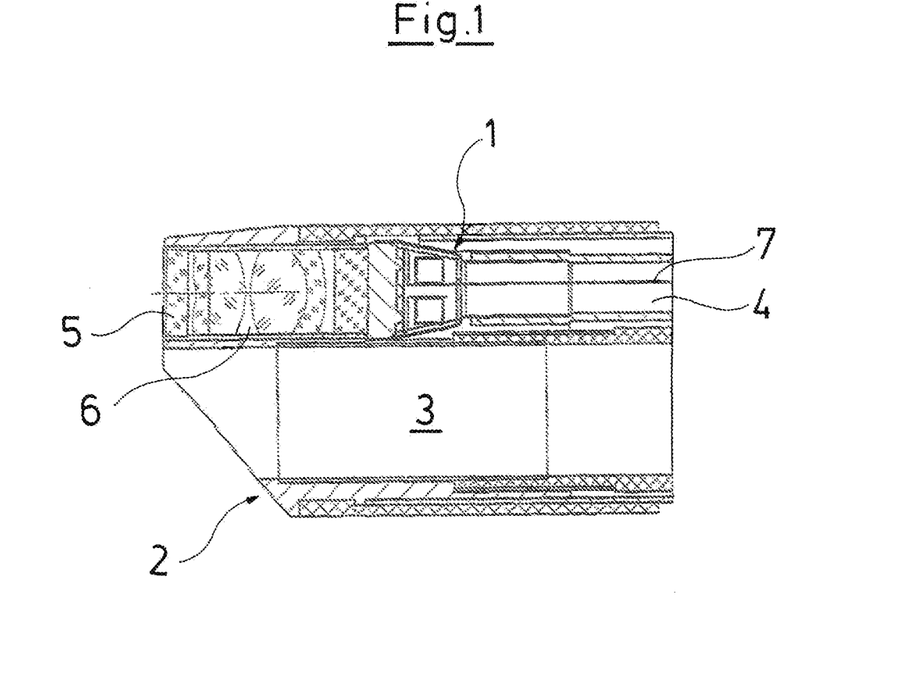
FIG. 1 is a greatly simplified schematic longitudinal section representation of the distal end of an endoscope.

The distal end of a video endoscope is represented in a longitudinal section by way of example in FIG. 1, and this distal end is equipped with a subassembly 1 according to the invention. In the figure, one can see the distal end section 2 with a working channel 3 and an optics channel 4 which is closed off at the end side by way of a window 5, e.g. of sapphire, which terminates the channel in a fixed and sealed manner. A lens 6 connects to this window 5 at the proximal side and is fixedly connected to the distal end of the subassembly 1 whose electrical connection cables in the form of individually insulated wires 12 surrounded by a shielding flexible sleeve and in the form of a cable 7 which is only schematically represented in FIG. 1 are led to the proximal instrument end.

Figure 2:
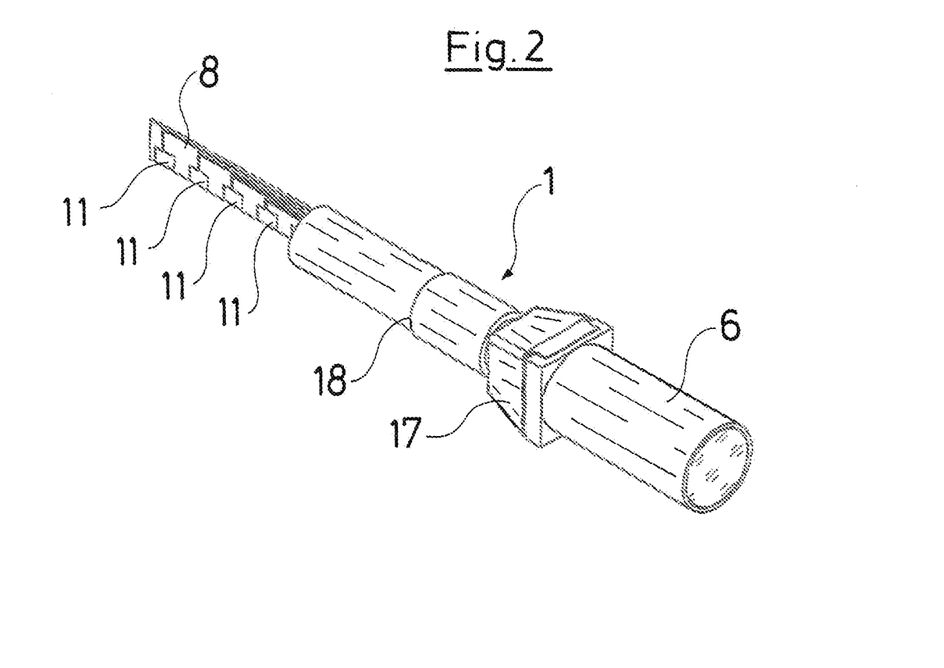
FIG. 2 is a perspective view from the front of a subassembly with a lens integrated in a housing.
Figure 3:
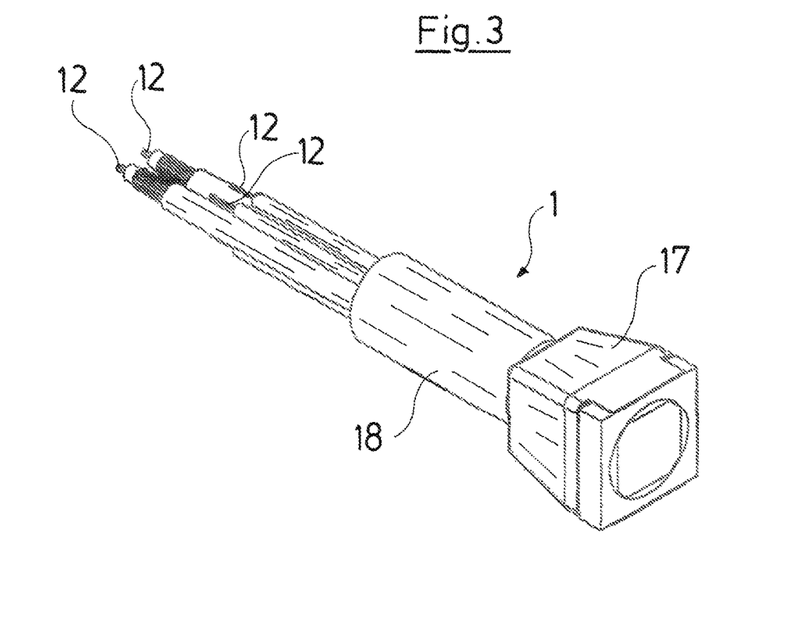
FIG. 3 is a front enlarged representation of the subassembly of FIG. 1, molded or cast into a housing with cables connected thereto.
Figure 4:
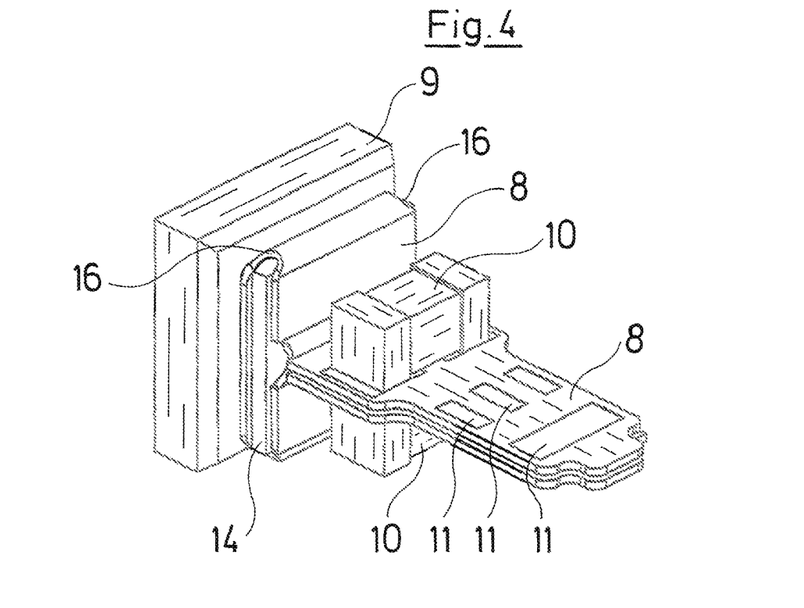
FIG. 4 is a perspective view from the rear of the subassembly without housing.

The subassembly 1 is represented by way of FIG. 2 (with lens) in a modified form and in FIG. 3 (without lens).

Figure 5:
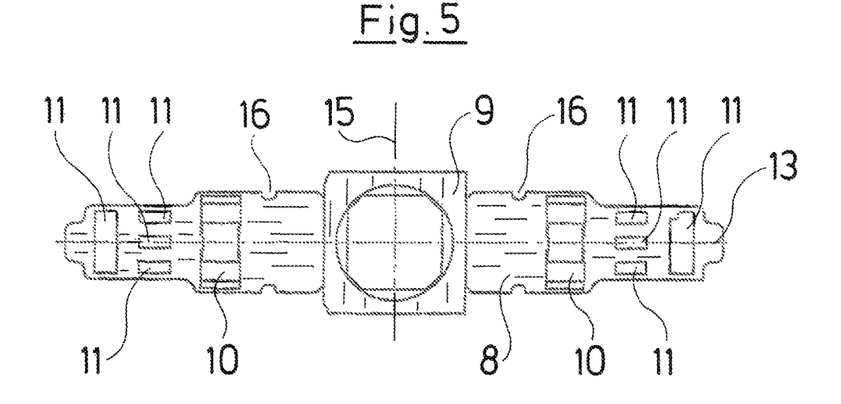
FIG. 5 is a plan view of the equipped circuit board, from the sensor side.
Figure 6:
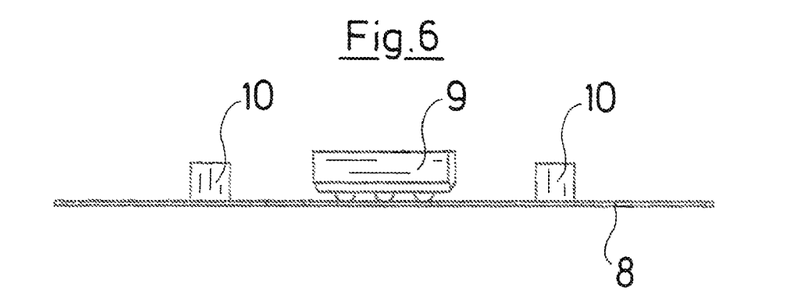
FIG. 6 is a lateral view of the equipped circuit board.

Such a subassembly 1 is constructed on a longitudinally extended, highly flexible circuit board 8, as is represented in FIGS. 4-7, and specifically in FIGS. 5 and 6 still in planar form, in which the equipping is effected. The circuit board 8 has an essentially longitudinally extended and rectangular shape. It is manufactured with thin-layer technology, wherein the leads within the circuit board and in particular also the contact surfaces on the upper side of the circuit board which is visible in FIG. 5, are formed by the layer-wise construction. In the present embodiment example, the circuit board has a thickness of 60 μm, and its width is slightly narrower than the picture-recording sensor 9 which is arranged thereon and whose rear-side contacts are electrically conductively connected to the upper side of the circuit board 8. Moreover, capacitors 10 are arranged on the upper side of the circuit board 8 and electrically conductively connected to this, on the upper side in the FIGS. 5 and 6 at a distance to the right and left of the sensor 9. Finally, electrical contacts 11, to which single-conductor, electrically insulated cables 12 are connected likewise via soldering, are provided on the upper side of the circuit board 8, wherein the subassembly 1 is electrically conductively connected to a proximally arranged (non-represented) control and evaluation unit via these cables.

The capacitors 10 which are arranged at a distance and parallel to the sensor 9 on the upper side of the circuit board 8 thus extend transversely to the longitudinal direction 13 of the circuit board 8.

Figure 7:
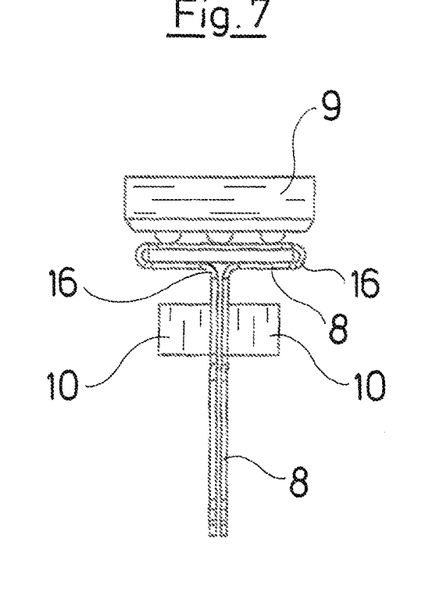
FIG. 7 is a top view of the equipped circuit board in a bent form/shape.

This circuit board 8 which is represented by way of the FIGS. 5 and 6 and which is completed with regard to its equipping, in the region of the sensor 9 and at the rear is provided with a reinforcement body 14 which with regard to its contour is slightly smaller than the sensor 9 and simultaneously forms a core, about which the circuit board 8 is bent as illustrated in FIG. 7. The circuit board thereby is bent about a bending line arranged parallel to the transverse axis 15, firstly by 90° at both sides of the reinforcement body 14, then follows the reinforcement body 14 over its height in this region, in order to be bent once again in each case by 90° at both sides and to then be led along the reinforcement body 14 to the middle at the rear. There, the circuit board 8 is again bent by 90° at both sides in a manner such that the free circuit board ends extend proximally from the middle of the reinforcement body 14, parallel to one another and roughly bearing on one anther which is to say contacting one another.

The bending locations which are weakened in cross section by the edge-side recesses 16 are arranged such that the reinforcement body 14 is almost completely surrounded by the middle part of the circuit board 8 at four sides. Thereby, the distance of the capacitors 10 to the sensor 9 is selected such that these, as can be recognized in FIGS. 4 and 7, in the bent condition of the circuit board 8 are arranged at a distance behind the region, in which the circuit board 8 surrounds the reinforcement body 14. The contacts 11 are arranged at the end of the circuit board 8, and these contacts are then arranged on two sides of the subassembly 1 which are opposite and away from one another due to the fact that the circuit board 8 runs out with its ends bearing on one another after the folding procedure.

Thereby, the cables 7, as described beforehand and represented by way of FIG. 3, can be soldered on the contacts 11. However, one can also envisage designing the circuit board such that this is as is represented by way of FIG. 2, i.e., such that all contacts lie one after the other seen in the longitudinal direction of the subassembly 1. The circuit board 8 can also be designed such that it forms the conductive connection up to the proximal end of the optics channel 4.

The unit which is represented by FIG. 7 and which consists of the circuit board 8 bent around the reinforcement body 14, equipped with the picture-recording sensor 9 as well as the capacitors 10 and the cables 12 connected to the contacts 11, is molded or cast into a housing 17 which laterally encompasses the sensor 9, is designed in a rectangular manner in this region and tapers proximally, in order there to merge into a cylindrical sleeve-like part 18. This housing 17 thus completely receives the construction unit represented in FIG. 4, to which construction unit it is fixedly and unreleasably connected by way of a molded or cast mass. Finally, the lens 6 is connected to the picture-recording side of the sensor 9, so that the subassembly 1 is completed, and this not only has extremely small radial dimensions, but also axial ones, if one just disregards the cables 12 which are significantly thinner in cross section. The thus formed subassembly 1 can be applied for flexible as well as for rigid endoscopes and in its radial dimensions is only insignificantly larger than the picture-providing sensor in the region of its active surface.

The subassembly 1 described above is equipped with a sensor 9 and two capacitors 10, as well as a multitude of contacts 11. It is to be understood that also other electrical or electric components can be arranged in this region proximally of the reinforcement body 14, instead of the capacitors 10, and the number and arrangement of the contacts 11 on the circuit board can be varied in a suitable manner.

Figure 8:
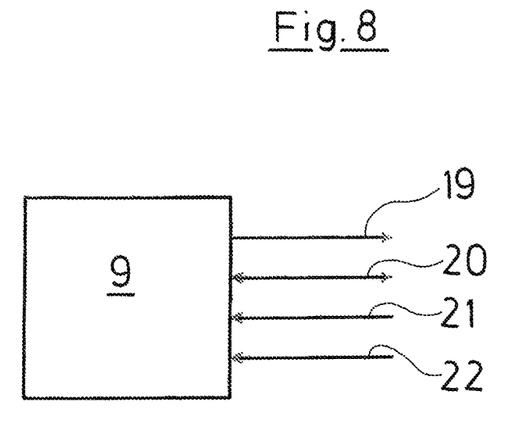
FIG. 8 is a block diagram of the subassembly.

A block circuit diagram for the connection of the sensor 9 is represented by way of FIG. 8. As is evident from this, this sensor on the one hand comprises the video output 19 which contains the actual picture signal, moreover a communication port 20 as well as an input 21 for the clock timing. A voltage supply 22 is finally present.

Figure 9:
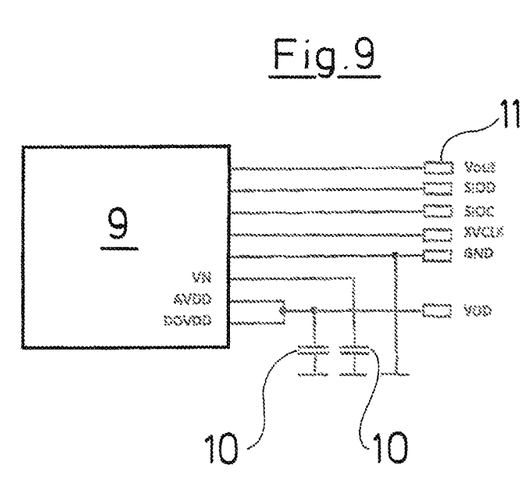
FIG. 9 is a circuit diagram of the subassembly.

The connections of the sensor 9 are specified in detail in the circuit diagram according to FIG. 9, and specified in this are:
Vout—video output signal
SIOC—communication channel
SIOD—communication channel
XVCLK—clock timing
GND—voltage supply
VDD—voltage supply
VN—voltage supply
AVDD—voltage supply
DOVDD—voltage supply The two capacitors 10 which here have a capacitance of 100 nF in each case are clearly visible in the circuit diagram according to FIG. 9.

Figure 10:
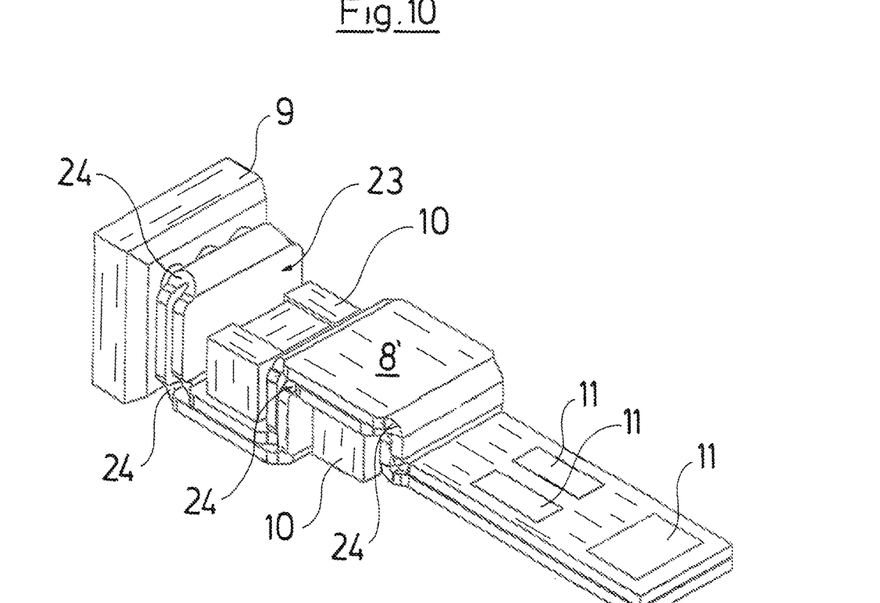
FIG. 10 is a perspective representation obliquely from the rear of a further embodiment of a subassembly according to the invention, without a housing.
Figure 11:
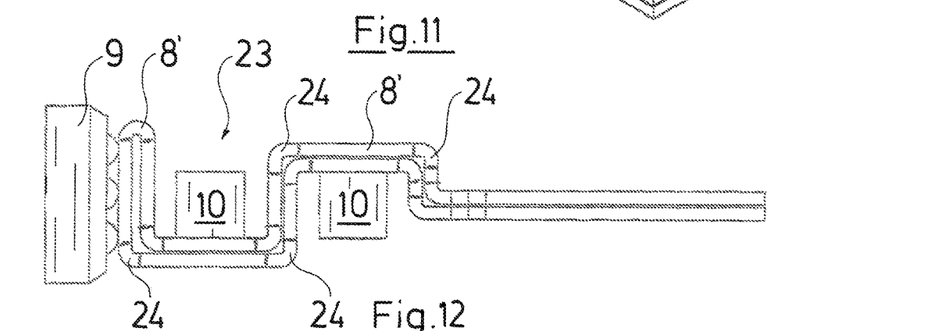
FIG. 11 is a lateral view of the subassembly according to FIG. 10.
Figure 12:
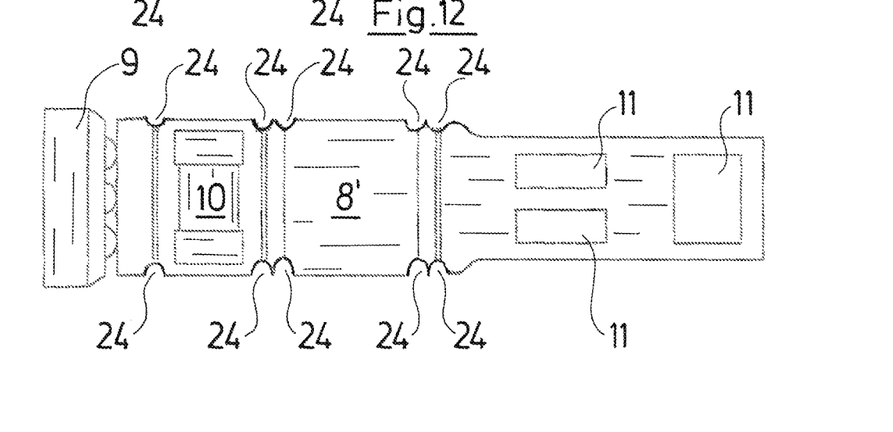
FIG. 12 is a plan view of the subassembly according to FIG. 10.

The subassembly represented by way of FIGS. 10-12 comprises a circuit board 8', with which it is the case of a highly flexible, 40 μm thick, single-layer circuit board which on one side is provided with strip conductors and by way of example comprises a sensor 9, two capacitors 10 as well as contacts 11 for connection to a cable 7. The circuit board 8' is bent at both sides of the sensor 9 and specifically at one side by 180° and at the other opposite side by 90°. The circuit board part which is bent by 180° runs at the rear of the circuit board part carrying the sensor 9, up to the circuit board part bend by 90°, where the other circuit board part is also bent proximally by 90°. A capacitor 10 is arranged in this region in an electrically conductive manner, on the circuit board part which is bent by 180° and subsequently by 90°. This capacitor 10 by way of example represents one or more electronic components. The circuit board parts which bear on one another below the capacitor 10 at the rear side are bent upwards by 90° proximally of this capacitor, in order then, after reaching the construction height of the first capacitor 10, to be bent again proximally by 90°. In this region, in which the free space is formed by an enveloping rectangular wave peak, the circuit board part which at the bottom there is equipped with a second capacitor 10, wherein this second capacitor is likewise representative by way of example, of one or more electronic components. All components 9, 10 as well as the electrical connections 11 which are arranged further proximally all lie on the same circuit board side, since the circuit board parts bear on one another at the rear, and the strip conductors are formed on the other side. These circuit board parts which bear on one another at the rear side are connected to one another by way of bonding and in a lateral view (FIG. 11) are led in a rectangular-wave-shaped manner, wherein electronic components are arranged in the free spaces 23 surrounded by a wave trough or a wave peak. The electronic components 10 as well as the circuit board parts of the circuit board 8' which are arranged behind the sensor 9, including the electrical contacts 11 of this circuit board and the cable connected there (not represented in the drawing) lie within the outer contour of the sensor 9, so that the dimensions of the sensor 9 determine the lumen of the subassembly. A particularly compact construction is ensured in the direction of the longitudinal axis of the subassembly since the bending by 90° and 180° lies within extremely tight bending radii, here of 40 μm. An extremely compact endoscope head therefore results after molding/casing the subassembly.

As to how the bending stress is reduced in the region of the bending of the circuit board 8' by way of recesses 24 in this region is visible by way of FIGS. 10 and 12. Such recesses are provided in a suitable size and number, in order to reduce the bending stress, usefully between strip conductors. If the arrangement of the strip conductors does not permit recesses between the strip conductors, then at least edge-side recesses 24 are to be provided, as these are realized with the subassemblies represented by way of the FIGS. 10-12.

While specific embodiments of the invention have been shown and described in detail to illustrate the application of the principles of the invention, it will be understood that the invention may be embodied otherwise without departing from such principles.

The invention claimed is:

1. A subassembly for a video endoscope, the subassembly comprising:
   at least one electrical cable;
   a flexible circuit board comprising a sensor portion adjacent to a subassembly distal end, a first cable portion extending towards a subassembly proximal end, a second cable portion extending towards the subassembly proximal end, a first bent portion connecting a first edge of the sensor portion to the first side cable portion, a second bent portion connecting the a second edge of the sensor portion to the second side cable portion, the sensor portion being perpendicular or nearly perpendicular to the first cable portion and to the second cable portion, at least one of the first cable portion and the second cable portion comprising an electrical contact electrically connected to the at least one electrical cable;
   a picture-recording sensor electrically conductively arranged on the flexible circuit board sensor portion; and
   a reinforcement body positioned in contact with the sensor portion and supporting the sensor portion, supporting the first bent portion and supporting the second bent portion of the flexible circuit board, whereby the first side cable portion and the second side cable portion are unsupported in a region between the first side cable portion and the second side cable portion allowing flexing of the first side cable portion and the second side cable portion.

2. A subassembly according to claim 1, further comprising at least one further electronic component, wherein the first bent portion or the second bent portion or both the first bent portion and the second bent portion carries the at least one further electronic component.

3. A subassembly according to claim 2, wherein the at least one further electronic component is a capacitor and is arranged on the circuit board in an electrically conductive manner in an end section or in a region of a free space of the first bent portion or the second bent portion or both the first bent portion and the second bent portion.

4. A subassembly according to claim 1, wherein the circuit board is bent several times at two sides which are opposite and away from one another.

5. A subassembly according to claim 1, wherein the circuit board carries the sensor and all further electronic components only on one circuit board side.

6. A subassembly according to claim 1, wherein the circuit board is a single-layer flex circuit board with a thickness between 40 μm and 100 μm.

7. A subassembly according to claim 1, wherein the circuit board is bent with a bending radius which corresponds to 0.5 to 2-fold the circuit board thickness.

8. A subassembly according to claim 1, wherein the at least one cable is electrically conductively connected to the circuit board at an end section or at end sections of the first bent portion or the second bent portion or both the first bent portion and the second bent portion of the circuit board.

9. A subassembly according to claim 8, further comprising a shielding sleeve, wherein circuit-board-side cable ends and the end section or end sections of the circuit board are surrounded by the shielding sleeve.

10. A subassembly according to claim 9, wherein a periphery of the sensor, the circuit board and the cable ends are molded in a plastic material that forms a surrounding housing.

11. A subassembly according to claim 1, wherein the circuit board is connected via single-conductor cables.

12. A subassembly according to claim 1, wherein:
the picture-recording sensor is attached to the sensor portion at a distal end side of the sensor portion;
the reinforcement body forms a core with a core side facing the sensor portion and contacting the sensor portion at an opposite side of the sensor portion, wherein the opposite side of the sensor portion is opposite to the distal end side of the sensor portion;
the circuit board is bent around the core with the first bent portion extending from the first edge of the sensor portion along a first side of the core and along a proximal end side of the core to the first side cable portion; and
the circuit board is bent around the core with the second bent portion extending from the second edge of the sensor portion along a second side of the core and along the proximal end side of the core to the first side cable portion.

13. A subassembly according to claim 12, wherein the core has a core contour that is slightly smaller than a contour of the picture-recording sensor.

14. An endoscope comprising a rigid or flexible shank with a subassembly comprising:
at least one electrical cable;
a flexible circuit board comprising a sensor portion adjacent to a subassembly distal end, a first cable portion extending towards a subassembly proximal end, a second cable portion extending towards the subassembly proximal end, a first bent portion connecting a first edge of the sensor portion to the first side cable portion, a second bent portion connecting a second edge of the sensor portion to the second side cable portion, the sensor portion being perpendicular or nearly perpendicular to the first cable portion and to the second cable portion, at least one of the first cable portion and the second cable portion comprising an electrical contact electrically connected to the at least one electrical cable;
a picture-recording sensor electrically conductively arranged on the flexible circuit board; and
a reinforcement body positioned in contact with the sensor portion and supporting the sensor portion, supporting the first bent portion and supporting the second bent portion of the flexible circuit board, whereby the first cable portion and the second cable portion are not supported by the reinforcement body to provide the first side cable portion and the second side cable portion with an unsupported region between the first side cable portion and the second side cable portion allowing flexing of the first side cable portion and the second side cable portion.

15. An endoscope according to claim 14, wherein:
the picture-recording sensor is attached to the sensor portion at a distal end side of the sensor portion;
the reinforcement body forms a core with a core side facing the sensor portion and contacting the sensor portion at an opposite side of the sensor portion, wherein the opposite side of the sensor portion is opposite to the distal end side of the sensor portion;
the circuit board is bent around the core with the first bent portion extending from the first edge of the sensor portion along a first side of the core and along a proximal end side of the core to the first side cable portion; and
the circuit board is bent around the core with the second bent portion extending from the second edge of the sensor portion along a second side of the core and along the proximal end side of the core to the first side cable portion.

16. An endoscope according to claim 15, wherein the core has a core contour that is slightly smaller than a contour of the picture-recording sensor.

17. An endoscope subassembly comprising:
an electrical cable;
a flexible circuit board comprising a sensor portion towards or adjacent to a subassembly distal end, cable portions extending towards or adjacent to a subassembly proximal end and bent portions connecting the sensor portion to the cable portions, the sensor portion being perpendicular or nearly perpendicular to the cable portions, one or both of the cable portions comprising an electrical contact electrically connected to the electrical cable;
an image capturing sensor electrically connected to and arranged on the sensor portion of the flexible circuit board; and
a reinforcement body positioned in contact with the sensor portion and supporting the sensor portion and supporting the bent portions, whereby the cable portions are not supported by the reinforcement body to provide each of the cable portions with an unsupported flexing region allowing flexing of the cable portion.

18. A subassembly according to claim 17, further comprising a further electronic component, wherein:
the cable portions have a further component portion between the sensor portion and the electrical contact, and the further electronic component is electrically connected to and arranged on the further component portion of the flexible circuit board.

19. A subassembly according to claim 18, wherein the sensor and the further electronic component are only connected to one circuit board side.

20. A subassembly according to claim 19, wherein the bent portions of the circuit board have at least one recess for reducing bending stress.

* * * * *